United States Patent [19]

Brown et al.

[11] Patent Number: 5,001,230

[45] Date of Patent: Mar. 19, 1991

[54] T CELL ACTIVATION MARKERS

[75] Inventors: Keith D. Brown, Hunters Hill, Australia; Timothy K. Mosmann, Atherton; Gerard Zurawski; Sandra M. Kurawski, both of Redwood City, Calif.

[73] Assignee: Schering Corporation, Kenilworth, N.J.

[21] Appl. No.: 157,743

[22] Filed: Feb. 18, 1988

[51] Int. Cl.$^5$ .............................................. C07H 17/00
[52] U.S. Cl. ...................................... 536/27; 536/28; 536/29
[58] Field of Search ............................. 536/27, 28, 29

[56] References Cited

U.S. PATENT DOCUMENTS 4,358,535  11/1982  Falkow et al. ........................... 435/5
4,483,920  11/1984  Gillespie et al. ......................... 435/6

FOREIGN PATENT DOCUMENTS 0194626  9/1986  European Pat. Off. .
0221768  5/1987  European Pat. Off. .
0260880  3/1988  European Pat. Off. .
87/03600  6/1987  World Int. Prop. O. .

OTHER PUBLICATIONS

Epes et al., Pnas, 85.9784–9708, 1888.
Angerer et al., Genetic Engineering, vol. 7, pp. 43–65, (1985).
Wolpe et al., J. Exp. Med., vol. 167, pp. 570–581 (1988).
Burd et al., J. Immunol., vol. 139, pp. 3126–3131 (1987).
White et al., J. Biol. Chem., vol. 257, pp. 8569–8572 (1982).
Southern, J. Mol. Biol. vol. 98, pp. 503–517 (1975).
Thomas, Proc. Natl. Acad. Sci., vol. 77, pp. 5201–5205 (1980).
Obaru et al., J. Biochem., vol. 99, pp. 885–894 (1986).

Primary Examiner—John W. Rollins
Attorney, Agent, or Firm—Stephen C. Macevicz

[57] ABSTRACT

A polypeptide designated H400 and its encoding nucleic acid are provided as markers specific for activated human T cells. Activated t cells are detected immunochemically by monoclonal antibodies specific for H400 or its immunogenic peptides. Activated T cells are also detected by nucleic acid probes directed to messenger RNA encoding the H400 protein.

2 Claims, 2 Drawing Sheets

```
CCCCCCCCAC AGGACACAGC TGGGTTCTGA AGCTTCTGAG TTCTGCAGCC

TCACCTCTGA GAAAACCTCT TTTCCACCAA TACC AGT AAG CTC TGC
                                      MET Lys Leu Cys

GTG ACT GTC CTG TCT CTC CTC ATG CTA GTA GCT GCC TTC TGC
Val Thr Val Leu Ser Leu Leu MET Leu Val Ala Ala Phe Cys

TCT CCA GCG CTC TCA GCA CCA ATG GGC TCA GAC CCT CCC ACC
Ser pro Ala Leu Ser Ala Pro MET Gly Ser Asp Pro Pro Thr GCC TGC TGC TTT TCT TAC ACC GCG AGG AAG CTT CCT CGC AAC
Ala Cys Cys Phe Ser Tyr Thr Ala Arg Lys Leu Pro Arg Asn TTT GTG GTA GAT TAC TAT GAG ACC AGC AGC CTC TGC TCC CAG
Phe Val Val Asp Tyr Tyr Glu Thr Ser Ser Leu Cys Ser Gln CCA GCT GTG GTA TTC CAA ACC AAA AGA AGC AAG CAA GTC TGT
Pro Ala Val Val Phe Gln Thr Lys Arg Ser Lys Gln Val Cys GCT GAT CCC AGT GAA TCC TGG GTC CAG GAG TAC GTG TAT GAC
Ala Asp Pro Ser Glu Ser Trp Val Gln Glu Tyr Val Tyr Asp CTG GAA CTG AAC TGAG    CTGCTCAGAG ACAGGAAGTC TTCAGGGAAG
Leu Glu Leu Asn

GTCACCTGAG CCCGGATGCT TCTCCATGAG ACACATCTCC TCCATACTCA

GGACTCCTCT CCGCAGTTCC TGTCCCTTCT CTTAATTTAA TCTTTTTTAT

GTGCCGTGTT ATTGTATTAG GTGTCATTTC CATTATTTAT ATTAGTTTAG

CCAAAGGATA AGTGTCCCCT ATGGATGGTC CACTGTCACT GTTTCTCTGC

TGTTGCAAAT ACATGGATAA CACATTTGAT TCGTGTGTGT TTTCATAATA

AAACTTTAAA
```

Figure 2

T CELL ACTIVATION MARKERS

FIELD OF THE INVENTION

The invention relates generally to methods and compositions for monitoring the status of the immune system; more particularly, the invention provides compositions for detecting activated T-cells by nucleic acid hybridization probes and/or immunochemical assays.

BACKGROUND

Regulation of normal immunologic reactivity involves the balance between positive and negative influences exerted by various subsets of T cells. Abnormally hyperactive and hypoactive T cells are believed to be associated with several immune disorders, including AIDS (hypoactivity and destruction of the helper T cell subset), and a variety of autoimmune disorders, such as MHC-associated autoimmune disease (e.g. lupus erythematosus) which is believed to be caused by excessive production of gamma interferon by T cells.

T cells have been identified by certain phenotypic cell surface markers. For example, the surface molecule T8, which is present on human T cells of the cytotoxic subset, can be detected by immunofluorescent staining using murine anti-human monoclonal antibodies, such as OKT8 (Ortho Diagnostics, Raritan, NJ) or Leu-2 (Becton-Dickinson, Mountain View, CA). However, such markers are, at best, only useful in measuring the size of subpopulations, they do not necessarily imply that the cells are secreting products associated with an activated state.

Many diagnostic assays have been developed which are based on either immunochemical detection of proteins, e.g. U.S. Pat. Nos. 4,562,003; 4,474,892; and 4,427,782; or the detection of nucleic acids, either RNA or DNA, present in or produced by target cells, e.g. Pettersson et al., Immunology Today, Vol. 6, pgs. 268–272 (1985); Falkow et al., U.S. Pat. No. 4,358,535; and Gillespie et al., U.S. Pat. No. 4,483,920. The latter assays use nucleic acid probes, usually fluorescently labeled or radioactively labeled DNAs or RNAs, which can be preferentially hybridized to complementary target nucleic acids in appropriately prepared samples or tissues. The assays can take a variety of forms, e.g. RNA blotting: Thomas, Proc. Natl. Acad. Sci., Vol. 77, pgs. 5201–5205 (1980); dot hybridization: White et al., J. Biol. Chem., Vol. 257, pgs. 8569–8572 (1982); Southern blotting: Southern, J. Mol. Biol., Vol. 98, pgs. 503–517; and in situ hybridization: Pinkel et al., Proc. Natl. Acad. Sci., Vol. 83, pgs. 2934–2938 (1986); and Angerer et al., Genetic Engineering, Vol. 7, pgs. 43–65 (1985).

In view of the present lack of convenient direct methods for measuring abnormal T cell activation, the availability of sensitive immunochemical assays or nucleic acid probes for detecting activated T cells would provide useful diagnostic tools.

SUMMARY OF THE INVENTION

The invention includes a mature human protein produced by activated T cells, designated herein as H400, and immunogenic peptides thereof, both of which are useful for generating antibodies employed in immunochemical assays for activated T cells. The amino acid sequence corresponding to the open reading frame encoding H400 is given in Formula I.

Formula I
Lys—Leu—Cys—Val—Thr—Val—Leu—Ser—
Leu—Leu—Met—Leu—Val—Ala—Ala—Phe—
Cys—Ser—Pro—Ala—Leu—Ser—Ala—Pro—
Met—Gly—Ser—Asp—Pro—Pro—Thr—Ala—
Cys—Cys—Phe—Ser—Tyr—Thr—Ala—Arg—Lys—
Leu—Pro—Arg—Ser—Asn—Phe—Val—Val—Asp—
Tyr—Tyr—Glu—Thr—Ser—Ser—Leu—Cys—
Ser—Gln—Pro—Ala—Val—Val—Phe—Gln—
Thr—Lys—Arg—Ser—Lys—Gln—Val—Cys—
Ala—Asp—Pro—Ser—Glu—Ser—Trp—Val—
Gln—Glu—Tyr—Val—Tyr—Asp—Leu—Glu—Leu—Asn The invention further includes monoclonal antibodies specific for the mature H400 protein and its immunogenic peptides, and nucleic acids encoding H400 and fragments thereof useful in the construction of nucleic acid probes for H400 messenger RNA (mRNA). The preferred nucleotide sequence of the open reading frame encoding H400 is given in Formula II.

A plasmid, designated herein as pcD(SRα)-H400, containing a cDNA insert capable of encoding H400 has been deposited with the American Type Culture Collection (Rockville, MD) under accession number 67614.

Formula II
ATG—AAG—CTC—TGC—GTG—ACT—GTC—CTG—
TCT—CTC—CTC—ATG—CTA—GTA—GCT—GCC—
TTC—TGC—TCT—CCA—GCG—CTC—TCA—GCA—
CCA—ATG—GGC—TCA—GAC—CCT—CCC—ACC—
GCC—TGC  TGC—TTT—TCT—TAC—ACC—GCG—AGG—
AAG—CTT—CCT—CGC—AAC—TTT—GTG—GTA—
GAT—TAC—TAT—GAG—ACC—AGC—AGC—CTC—
TGC—TCC—CAG—CCA—GCT—GTG—GTA—TTC—
CAA—ACC—AAA—AGA—AGC—AAG—CAA—GTC—
TGT—GCT—GAT—CCC—AGT—GAA—TCC—TGG—
GTC—CAG—GAG—TAC—GTG—TAT—GAC—CTG—
GAA—CTG—AAC As used herein, the term "mature" in reference to protein H400 means the secreted form of H400. That is, the form of H400 that results from proteolytic cleavage of the signal peptide.

As used herein, "immunogenic peptide" in reference to H400 means a peptide (1) which consists of from 6 to 40 amino acids having a sequence identical to an equal length portion of mature H400 and (2) which in conjugation with a carrier protein is capable of eliciting antibodies which cross react with mature H400.

As used herein, "nucleic acid fragment" means a nucleic acid which consists of from about 18 to 264 nucleotides having a sequence complementary to an equal length portion of the nucleic acid defined by Formula II.

BRIEF DESCRIPTION OF THE DRAWINGS

FIG. 2 lists the nucleotide sequence of the cDNA insert of pcD(SRα)-H400 and indicates the amino acid sequence corresponding to the largest open reading frame.

DETAILED DESCRIPTION OF THE INVENTION

Figure 1:
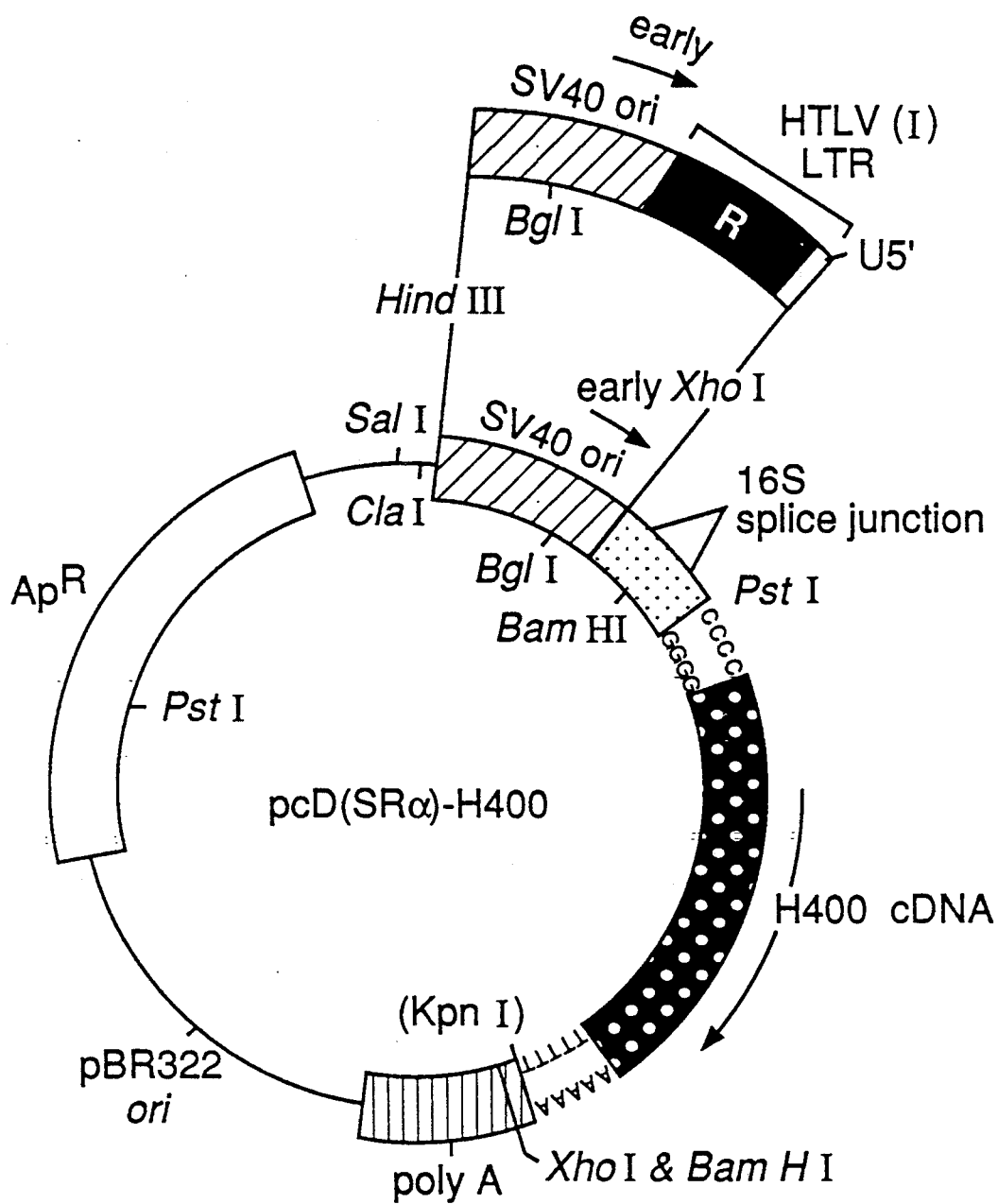
FIG. 1 diagrammatically illustrates the plasmid pcD(SRα)-H400 and selected restriction sites.

The invention is based on the discovery of a novel protein, H400, which is produced specifically by activated T cells. The protein H400 is encoded by the largest open reading frame of the cDNA insert of pcD(SRα)-H400. The invention is directed to compounds useful in detecting cells which either produce the H400 protein or produce mRNA transcripts capable of encoding the H400 protein. These compounds include the mature protein H400, immunogenic peptides thereof, monoclonal antibodies specific for mature H400 or its immunogenic peptides, nucleic acids capable of encoding H400, and nucleic acid fragments for constructing nucleic acid probes specific for mRNA which encodes H400.

I. Production of Mature H400

H400 can be produced by expressing a nucleotide sequence encoding it in a suitable expression system. Possible types of host cells include, but are not limited to, bacterial, yeast, insect, mammalian, and the like. Selecting an expression system, and optimizing protein production thereby, involves the consideration and balancing of many factors, including (1) the nature of the protein to be expressed, e.g. the protein may be poisonous to some host organisms, it may be susceptible to degradation by host proteases, or it may be expressed in inactive conformations or in insoluble form in some hosts, (2) the nature of the messenger RNA (mRNA) corresponding to the protein of interest, e.g. the mRNA may have sequences particularly susceptible to host endonucleases, which drastically reduce the functional lifetime of the mRNA, or the mRNA may form secondary structures that mask the start codon or ribosome binding site, thereby inhibiting translation initiation in some hosts, (3) the selection, availability, and arrangement of host-compatible expression control sequences in the 3' and 5' regions flanking the coding region— these include promoters, 5' and 3' protector sequences, ribosome binding sites, transcription terminators, enhancers, polyadenylate addition sites, cap sites, intron-splice sites, and the like, (4) whether the protein has a secretion signal sequence which can be processed by the host, or whether an expression control sequence encoding a signal sequence endogenous to the host must be spliced onto the region encoding the mature protein, (5) the available modes and efficiencies of transfection or transformation of the host, and whether transient or stable expression is desired, (6) the scale and cost of the host culture system desired for expressing the protein, (7) whether, and what type of, posttranslational modifications are desired, e.g. the extent and kind of glycosylation desired may affect the choice of host, (8) the ease with which the expressed protein can be separated from proteins and other materials of the host cells and/or culture medium e.g. in some cases it may be desirable to express a fusion protein with a specialized signal sequence to aid in later purification steps, e.g. Sassenfeld et al., *Biotechnology*, January 1984, (9) the stability and copy number of a particular vector in a selected host, e.g. Hofschneider et al., eds. *Gene Cloning in Organisms Other than E. Coli* (Springer Verlag, Berlin, 1982), and (10) like factors known to those skilled in the art.

Many reviews are available which provide guidance for making choices and/or modifications of specific expression systems in light of the recited factors, e.g. to name a few, de Boer and Shepard, "Strategies for Optimizing Foreign Gene Expression in Escherichia coli," pgs. 205–247, in Kroon, ed. *Genes: Structure and Expression* (John Wiley & Sons, New York, 1983), review several *E. coli* expression systems; Kucherlapati et al., *Critical Reviews in Biochemistry*, Vol. 16, Issue 4, pgs. 349–379 (1984), and Banerji et al., *Genetic Engineering*, Vol. 5, pgs. 19–31 (1983) review methods for transfecting and transforming mammalian cells; Reznikoff and Gold, eds., *Maximizing Gene Expression* (Butterworths, Boston, 1986) review selected topics in gene expression in *E. coli*, yeast, and mammalian cells; and Thilly, *Mammalian Cell Technology* (Butterworths, Boston, 1986) reviews mammalian expression systems.

Likewise, many reviews are available which describe techniques and conditions for linking and/or manipulating specific cDNAs and expression control sequences to create and/or modify expression vectors suitable for use with the present invention, e.g. Maniatis et al., *Molecular Cloning: A Laboratory Manual* (Cold Spring Harbor Laboratory, N.Y., 1982); Glover, *DNA Cloning: A Practical Approach*, Vol. I and II (IRL Press, Oxford, 1985), and Perbal, *A Practical Guide to Molecular Cloning* (John Wiley & Sons, N.Y., 1984), to name only a few. Generally, within an expression vector various sites may be selected for insertion of the cDNA of the invention. These sites are usually designated by the restriction endonuclease which cuts them and are well recognized by those of skill in the art. Various methods for inserting DNA sequences into these sites to form recombinant DNA molecules are also well known. These include, for example, dG-dC or dA-dT tailing, direct ligation, synthetic linkers, exonuclease and polymerase-linked repair reactions followed by ligation, or extension of the DNA strand with DNA polymerase and an appropriate single-stranded template followed by ligation.

Often a vector containing the cDNA of the invention must be obtained in large quantities before transfection and/or transformation of cells in a host culture can take place. For this purpose the vector is often replicated without significant expression in an organism (the cloning host) other than the one finally used for expression. In such cases, after propagation, the vectors are separated from the cloning host using standard techniques, e.g. as disclosed in Maniatis et al. (cited above).

Preferably H400 is produced by expressing the H400 cDNA carried by pcD(SRα)-H400 in a host cell suitable for pcD vectors, e.g. COS monkey cells (available from the ATCC under accession numbers CRL 1650 or CRL-1651), C127 mouse mammary tumor cell (available from ATCC under accession number CRL 1616), or mouse L cells. Eukaryotic hosts are capable of cleaving the signal peptide from the freshly translated H400 polypeptide to form the mature H 400 polypeptide. Eukaryotic hosts are also capable of producing other posttranslation modifications, such as glycosylation, which may be antigenically important.

Production of H400 in a bacterial expression system requires that the cleavage site of the signal peptide be determined, either for direct expression of a nucleic acid encoding the mature H400 polypeptide or for linking such as nucleic acid to a bacterial sequence encoding an endogenous signal peptide. Empirical rules have been developed for making such predictions with a high degree of accuracy, e.g. von Heijne, *Eur. J. Biochem.*, Vol. 133, pgs. 17–21 (1983); *J. Mol. Biol.*, Vol. 184, pgs. 99–105 (1985); *Nucleic Acids Research*, Vol. 14, pgs. 4683–4690 (1986); and Perlman et al., *J. Mol. Biol.*, Vol. 167, pgs. 391–409 (1983). von Heijne's rules indicate that mature H400 begins with the alanine of position 23 with respect to the N-terminal amino acid of Formula I (the predicted mature sequence is illustrated below in Formula III).

Mature H400 is produced as follows by COS7 cells transiently transfected with pcD(SRα)-H400. One day prior to transfection, approximately $10^6$ COS 7 monkey cells are seeded onto individual 100 mm plates in Dulbecco's modified Eagle medium (DME) containing 10% fetal calf serum and 2 mM glutamine. To perform the transfection, the medium is aspirated from each plate and replaced with 4 ml of DME containing 50 mM Tris.HCl pH 7.4, 400 μg/ml DEAE-Dextran and 50 μg of the plasmid DNAs to be tested. The plates are incubated for four hours at 37° C., then the DNA-containing medium is removed, and the plates are washed twice with 5 ml of serum-free DME. DME is added back to the plates which are then incubated for an additional 3 hrs at 37° C. The plates are washed once with DME and then DME containing 4% fetal calf serum, 2 mM glutamine, penicillin and streptomycin is added. The cells are then incubated for 72 hrs at 37° C. The growth medium is collected and H400 purified therefrom using standard methods.

II. Immunogenic Peptides of H400

The present invention includes peptides derived from mature H400 which form immunogens when conjugated with a carrier. The term immunogen as used herein refers to a substance which is capable of causing an immune response. The term carrier as used herein refers to any substance which when chemically conjugated to a peptide of the invention permits a host organism immunized with the resulting conjugate to generate antibodies specific for the conjugated peptide. Carriers include red blood cells, bacteriophages, proteins, or synthetic particles such as agarose beads. Preferably carriers are proteins, such as serum albumin, gamma-globulin, keyhole limpet hemocyanin, thyroglobulin, ovalbumin, fibrinogen, or the like.

Peptides of the invention are defined in terms of their positions within the following amino acid sequence of mature H400:

Formula III
Ala—Pro—Met—Gly—Ser—Asp—Pro—Pro—

Thr—Ala—Cys—Cys—Phe—Ser—Tyr—Tyr—

Ala—Arg—Lys—Leu—Pro—Arg—Asn—Phe—Val—

Val—Asp—Tyr—Tyr—Glu—Thr—Ser—Ser—

Leu—Cys—Ser—Gln—Pro—Ala—Val—Val—

Phe—Gln—Thr—Lys—Arg—Ser—Lys—Gln—

Val—Cys—Ala—Asp—Pro—Ser—Glu—Ser—

-continued
Formula III

Trp—Val—Gln—Glu—Tyr—Val—Tyr—Asp—.

Leu—Glu—Leu—Asn

Amino acids of Formula III are numbered with respect to the N-terminus of the mature H400 polypeptide. Thus, $Ser_5$ is serine at position 5. Peptides are defined as fragments of the mature H400 polypeptide. Thus, the peptide designated herein by $Ser_5$-$Cys_{11}$ is equivalent to the peptide Ser-Asp-Pro-Thr-Ala-Cys. Groups of peptides of the invention are also defined in terms of fragments of the mature H400 polypeptide. Thus, the group designated herein as $[Ser_5$-$Cys_{11}]_{5-6}$ consists of all 5 and 6 amino acid peptides (i.e. all 5-mers and 6-mers) whose sequences are identical to all or part of the peptide $Ser_5$-$Cys_{11}$. That is, the group consists of the following five peptides: Ser-Asp-Pro-Pro-Thr-Ala, Asp-Pro-Pro-Thr-Ala-Cys, Ser-Asp-Pro-Pro-Thr, Asp-Pro-Pro-Thr-Ala, and Pro-Pro-Thr-Ala-Cys.

Generally the invention includes all 6-mer to 24-mer peptide fragments of mature H400, i.e. $[Ala_1$-$Glu_{66}]_{6-24}$. Preferably, the invention includes 6-mer to 24-mer peptide fragments which include the N-terminal or C-terminal sequences of the mature H400 polypeptide, or which correspond to sequences of the mature H400 polypeptide that have high average hydrophilicity, as determined by Hopp-Woods or related analysis, e.g. Hopp and Woods, *Proc. Natl. Acad. Sci.*, Vol. 78, pgs. 3824–3828 (1981); or Kyte and Doolittle, *J. Mol. Biol.*, Vol. 157, pgs. 105–132 (1982). The latter set of preferred peptides of the invention includes the following groups: $[Ala_1$-$Ser_{20}]_{6-20}$ and $[Thr43$-$Glu_{66}]_{6-24}$.

Standard symbols are used throughout for amino acids, e.g. Cohen, "Nomenclature and Symbolism of alpha-Amino Acids," *Methods in Enzymology*, Vol. 106, pgs. 3–17 (Academic Press, N.Y., 1984). Accordingly, Table I of this reference is incorporated by reference.

Peptides of the invention are synthesized by standard techniques, e.g. Stewart and Young, *Solid Phase Peptide Synthesis*, 2 nd Ed. (Pierce Chemical Company, Rockford, IL, 1984). Preferably a commercial automated synthesizer is used, e.g. Vega Biochemicals (Tucson, AZ) models 296A or B, or Applied Biosystems, Inc. (Foster City, CA) model 430A.

Peptides of the invention are assembled by solid phase synthesis on a cross-linked polystyrene support starting from the carboxyl terminal residue and adding amino acids in a stepwise fashion until the entire 34 residue chain had been formed. The synthesis was performed on a fully automated peptide synthesizer (Applied Biosystems, Inc. model 430A). The following references are guides to the chemistry employed during synthesis: Merrifield, *J. Amer. Chem. Soc.*, Vol. 85, pg. 2149 (1963); Kent et al., pg 185, in *Peptides* 1984, Ragnarsson, Ed. (Almquist and Weksell, Stockholm, 1984); Kent et al., pg. 217 in *Peptide Chemistry* 84, Izumiya, Ed. (Protein Research Foundation, B. H. Osaka, 1985); Merrifield, *Science*, Vol. 232, pgs. 341–347 (1986); and references cited in this latter reference.

In solid state synthesis it is most important to eliminate synthesis by-products, which are primarily termination, deletion, or modification peptides. Most side reactions can be eliminated or minimized by use of clean, well characterized resins, clean amino acid derivatives, clean solvents, and the selection of proper coupling and cleavage methods and reaction conditions, e.g. Barany and Merrifield, *The Peptides*, Cross and Meienhofer, Eds., Vol. 2, pgs 1–284 (Academic Press, N.Y., 1979). It is important to monitor coupling reactions to determine that they proceed to completion so that deletion peptides missing one or more residues will be avoided. The quantitative ninhydrin reaction is useful for that purpose, Sarin et al. *Anal. Biochem*, Vol. 117, pg 147 (1981). Nα-t-butyloxycarbonyl (t-Boc)-amino acids were used with appropriate side chain protecting groups stable to the conditions of chain assembly but labile to strong acids. After assembly of the protected peptide chain, the protecting groups were removed and the peptide anchoring bond was cleaved by the use of low then high concentrations of anhydrous hydrogen fluoride in the presence of a thioester scavenger, Tam et al., *J. Amer. Chem. Soc.*, Vol. 105, pg. 6442 (1983).

Side chain protecting groups used were Asp(OBzl), Glu(OBzl), Ser(Bzl), Thr(Bzl), Lys(Cl-Z), Tyr(Br-Z), Arg(N$^G$Tos), Cys(4-MeBzl), and His(ImDNP). (Bzl, benzyl; Tos toluene sulfoxyl; DNP, dinitrophenyl; Im, imidazole; Z, benzyloxycarbonyl. The remaining amino acids had no side chain protecting groups. All the amino acids were obtained from Peninsula Laboratories, except the tBoc-His(ImDNP), which was from Chemical Dynamics and was crystallized from ethanol before use. For each cycle the tBoc Nα protected peptide-resin was exposed to 65 percent trifluoroacetic acid (from Eastman Kodak) (distilled before use) in dichloromethane (DCM), (Mallenckrodt): first for 1 minute then for 13 minutes to remove the Nα-protecting group. The peptide-resin was washed in DCM, neutralized twice with 10 percent diisopropylethylamine (DIEA) (Aldrich) in dimethylformamide (DMF) (Applied Biosystems), for 1 minute each. Neutralization was followed by washing with DMF. Coupling was performed with the preformed symmetric anhydride of the amino acid in DMF for 16 minutes. The preformed symmetric anhydride was prepared on the synthesizer by dissolving 2 mmol of amino acid in 6 ml of DCM and adding 1 mmol of dicyclohexycarbodiimide (Aldrich) in 2 ml of DCM. After 5 minutes, the activated amino acid was transferred to a separate vessel and the DCM was evaporated by purging with a continuous stream of nitrogen gas. The DCM was replaced by DMF (6 ml total) at various stages during the purging. After the first coupling, the peptide-resin was washed with DCM, 10 percent DIEA in DCM, and then with DCM. For recoupling, the same amino acid and the activating agent, dicyclohexylcarbodiimide, were transferred sequentially to the reaction vessel. After activation in situ and coupling for 10 minutes, sufficient DMF was added to make a 50 percent DMF-DCM mixture, and the coupling was continued for 15 minutes. Arginine was coupled as a preformed hydroxybenzotriazole (Aldrich) ester in DMF for 60 minutes and then recoupled in the same manner as the other amino acids. Asparagine and glutamine were coupled twice as preformed hydroxybenzotriazole esters in DMF, 40 minutes for each coupling. For all residues, the resin was washed after the second coupling and a sample was automatically taken for monitoring residual uncoupled α-amine by quantitative ninhydrin reaction, Sarin et al. (cited above).

The general technique of linking synthetic peptides to a carrier is described in several references, e.g. Walter and Doolittle, "Antibodies Against Synthetic Peptides," in Setlow et al., eds., *Genetic Engineering*, Vol. 5, pgs. 61–91 (Plenum Press, N.Y., 1983); Green et al. *Cell*, Vol. 28, pgs. 477–487 (1982); Lerner et al., *Proc. Natl. Acad. Sci.*, Vol. 78, pgs. 3403–3407 (1981); Shimizu et al., U.S. Pat. No. 4,474,754; and Ganfield et al., U.S. Pat. No. 4,311,639. Accordingly, these references are incorporated by reference. Also, techniques employed to link haptens to carriers are essentially the same as the above-referenced techniques, e.g. chapter 20 in Tijsseu *Practice and Theory of Enzyme Immunoassays* (Elsevier, New York, 1985).

The four most commonly used schemes for attaching a peptide to a carrier are (1) glutaraldehyde for amino coupling, e.g. as disclosed by Kagan and Glick, in Jaffe and Behrman, eds. *Methods of Hormone Radioimmunoassay*, pgs. 328–329 (Academic Press, N.Y., 1979), and Walter et al. *Proc. Natl. Acad. Sci.*, Vol. 77, pgs. 5197–5200 (1980); (2) water-soluble carbodiimides for carboxyl to amino coupling, e.g. as disclosed by Hoare et al., *J. Biol. Chem.*, Vol. 242, pgs. 2447–2453 (1967); (3) bis-diazobenzidine (BDB) for tyrosine to tyrosine sidechain coupling, e.g. as disclosed by Bassiri et al., pgs. 46–47, in Jaffe and Behrman, eds. (cited above), and Walter et al. (cited above); and (4) maleimidobenzoyl-N-hydroxysuccinimide ester (MBS) for coupling cysteine (or other sulfhydryls) to amino groups, e.g. as disclosed by Kitagawa et al., *J. Biochem.* (Tokyo), Vol. 79, pgs. 233–239 (1976), and Lerner et al. (cited above).

A general rule for selecting an appropriate method for coupling a given peptide to a protein carrier can be stated as follows: the group involved in attachment should occur only once in the sequence, preferably at the appropriate end of the segment. For example, BDB should not be used if a tyrosine residue occurs in the main part of a sequence chosen for its potentially antigenic character. Similarly, centrally located lysines rule out the glutaraldehyde method, and the occurrences of aspartic and glutamic acids frequently exclude the carbodiimide approach. On the other hand, suitable residues can be positioned at either end of chosen sequence segment as attachment sites, whether or not they occur in the "native" protein sequence.

Internal segments, unlike the amino and carboxy termini, will differ significantly at the "unattached end" from the same sequence as it is found in the native protein where the polypeptide backbone is continuous. The problem can be remedied, to a degree, by acetylating the α-amino group and then attaching the peptide by way of its carboxy terminus.

The coupling efficiency to the carrier protein is conveniently measured by using a radioactively labeled peptide, prepared either by using a radioactive amino acid for one step of the synthesis or by labeling the completed peptide by the iodination of a tyrosine residue. The presence of tyrosine in the peptide also allows one to set up a sensitive radioimmune assay, if desirable. Therefore, tyrosine can be introduced as a terminal residue if it is not part of the peptide sequence defined by the native H400 polypeptide.

Preferred carriers are proteins, and preferred protein carriers include bovine serum albumin, myoglobulin, ovalbumin (OVA), keyhole limpet hemocyanin (KLH), or the like.

Peptides can be linked to KLH through cysteines by MBS as disclosed by Liu et al., *Biochemistry*, Vol. 18, pgs. 690–697 (1979). The peptides are dissolved in phosphate-buffered saline (pH 7.5), 0.1M sodium borate buffer (pH 9.0) or 1.0M sodium acetate buffer (pH 4.0). The pH for the dissolution of the peptide is chosen to optimize peptide solubility. The content of free cysteine for soluble peptides is determined by Ellman's method, Ellman, *Arch. Biochem. Biophys.*, Vol. 82, pg. 7077 (1959).

For each peptide, 4 mg KLH in 0.25 ml of 10 mM sodium phosphate buffer (pH 7.2) is reacted with 0.7 mg MBS (dissolved in dimethyl formamide) and stirred for 30 min at room temperature. The MBS is added dropwise to ensure that the local concentration of formamide is not too high, as KLH is insoluble in $\geq 30\%$ formamide. The reaction product, KLH-MB, is then passed through Sephadex G-25 equilibrated with 50 mM sodium phosphate buffer (pH 6.0) to remove free MBS, KLH recovery from peak fractions of the column eluate (monitored by $OD_{280}$) is estimated to be approximately 80%.

KLH-MB is then reacted with 5 mg peptide dissolved in 1 ml of the chosen buffer. The pH is adjusted to 7–7.5 and the reaction is stirred for 3 hr at room temperature. Coupling efficiency is monitored with radioactive peptide by dialysis of a sample of the conjugate against phosphate-buffered saline, and ranged from 8% to 60%.

III. Monoclonal Antibodies and Immunochemical Assays

Monoclonal antibodies are produced against mature H400 or peptide-carrier conjugates by standard techniques, e.g. as disclosed by Campbell *Monoclonal Antibody Technology* (Elsevier, N.Y., 1984); Hurrell, ed. *Monoclonal Hybridoma Antibodies: Techniques and Applications* (CRC Press, Boca Raton, Fla., 1982); Schreier et al. *Hybridoma Techniques* (Cold Spring Harbor Laboratory, New York, 1980); U.S. Pat. No. 4,562,003; or the like. In particular, U.S. Pat. No. 4,562,003 is incorporated by reference. For monoclonal antibody production, the first step is to immunize a host animal to obtain a source of B lymphocytes. The B lymphocytes are fused with an appropriate immortalizing cell line to form monoclonal antibody secreting hybridomas. Immortalizing cell lines are usually tumor cell lines, such as myelomas. Preferably, the host animals are rodents, and the immortalizing cell line is derived from rodent cells. More preferably they are from the same species. After formation, hybridomas are screened for those producing antibodies against the peptide of the invention. Immunization, lymphocyte harvesting, and cell fusion are all technique well known in the art. Roughly, immunization is carried out by a regimen of repeated injections into the host animal of the purified peptide-carrier conjugate, usually mixed with a suitable adjuvant. Immunization can be optimized by varying several factors, including the amount of antigen used for the primary injection and subsequent boosts, the route of injection, the time schedule for injecting and bleeding, and the use of adjuvant, e.g. Freund's complete or incomplete adjuvant. Techniques for fusion are also well known in the art, and in general, involve mixing the cells with a fusing agent such as, most commonly, polyethylene glycol.

Successful hybridoma formation is assessed and selected by standard procedures such as, for example, HAT selection. From among successful hybridomas, those successfully secreting the desired antibody are selected by assaying the culture medium for their presence. Ordinarily this is done using immunoreaction based assays, including, without limitation, Western blot, ELISA, or RIA assays. The antibodies can be recovered from the medium using standard protein purification techniques.

"Two site" or "sandwich" immunoassays are the preferred immunoassays of the invention, e.g. as disclosed in U.S. Pat. No. 4,486,530. Accordingly, this patent is incorporated by reference. Such assays entail the use of two different sets of anti-H400 antibodies, at least one of which consists of a monoclonal antibody of the invention. Antibodies from one of the two sets are attached to the surface of a solid phase support. The attached antibodies are then exposed to a sample suspected of containing H400. The H400 molecules bind to the attached antibodies. Next, the second set of antibodies is applied to the bound H400, and binds to one or more antigenic determinants distinct from that (or those) to which the first set of antibodies is (or are) bound. The H400 is then detected by an indirect or direct signal generating means associated with the second set of antibodies. For example, the antibodies can be directly conjugated to a signal generating moiety, such as an enzyme, rare earth chelator, or an organic dye. Or, they can be indirectly linked to one or more signal generating moieties via additional antibodies, or high affinity complexes, such as the avidin-biotin complexes. Quantitative measures of H400 concentration are made by comparing the signal generated by the sample to signals generated by H400 standards containing known concentrations of H400.

The invention includes kits of reagents for use in immunoassays, particularly sandwich immunoassays. Such kits include (1) a solid phase support, (2) a first antibody which is monoclonal and which is capable of binding to a first antigenic determinant of H400, (3) a second antibody selected from the group consisting of a monoclonal antibody capable of binding to a second antigenic determinant of H400 and a polyclonal antibody specific for H400 (referred to herein as a "polyclonal antibody composition"), and (4) a signal generation means associated with one of the three antibodies. Depending on the particular embodiment, kits may include a selection of two of the three anti-H400 antibody types, either a monoclonal antibody specific for a first antigenic determinant and a monoclonal antibody specific for a second antigenic determinant, or a monoclonal antibody specific for a first or second antigenic determinant and a polyclonal antibody composition. The antibodies may be in solution or in lyophilized form. One of the sets of antibodies may come pre-attached to the solid support, or may be applied to the surface of the solid support when the kit is used. The signal generating means may come pre-associated with one of the two antibody types, or may require combination with one or more components, e.g. buffers, antibody-enzyme conjugates, enzyme substrates, or the like, prior to use. Many types of signal generating means are available and could make up one or more components of a kit. Various signal generating means are disclosed by Tijssen, *Practice and Theory of Enzyme Immunoassays* (Elsevier, Amsterdam, 1985). Kits of the invention may also include additional reagents, e.g. blocking reagents for reducing nonspecific binding to the solid phase surface, washing reagents, enzyme substrates, and the like. The solid phase surface may be in the form of microtiter plates, microspheres, or the like, composed of polyvinyl chloride, polystyrene, or the like materials suitable for immobilizing proteins. Such materials having solid phase surfaces are referred to herein as "support means". Preferably, an enzyme which catalyzes the formation of a fluorescent or colored product is a component of the signal generating means. More preferably, the enzyme is selected from the group consisting of peroxidase, alkaline phosphatase, and beta-galactosidase. Substrates and reaction conditions for these enzymes are well known in the art, e.g. Tijssen (cited above).

IV. Nucleic Acid Probes

Nucleic Acid probes of the invention are constructed from nucleotide sequences determined by the nucleic acid of Formula II. The nature of the probe and its associated nucleic acid can vary depending on the particular hybridization assay employed. One method of measuring H400 mRNA is by cytoplasmic dot hybridization as described by White et al., *J. Biol. Chem.*, Vol. 257, pgs. 8569–8572 (1982) and Gillespie et al., U.S. Pat. No. 4,483,920. Accordingly, these references are incorporated by reference. Other approaches include in situ hybridization, e.g. Angerer et al., *Genetic Engineering*, Vol. 7, pgs. 43–65 (1985), and dot blotting using purified RNA, e.g. chapter 6, in Hames et al., eds., *Nucleic Acid Hybridization A Practical Approach* (IRL Press, Washington, D.C., 1985). Generally, cytoplasmic dot hybridization involves anchoring mRNA from a cell or tissue sample onto a solid phase support, e.g. nitrocellulose, hybridizing a DNA probe to the anchored mRNA, and removing probe sequences nonspecifically bound to the solid phase support or forming mismatched hybrids with the mRNA so that only probe sequences forming substantially perfect hybrids with target mRNAs remain. The amount of DNA probe remaining is a measure of the number of target mRNA anchored to the solid phase support. The amount of DNA probe remaining is determined by the signal generated by its label.

Several standard techniques are available for labeling single and double stranded nucleic acid fragments. They include incorporation of radioactive labels, e.g. Harper et al., *Chromosoma*, Vol. 83, pgs. 431–439 (1984); direct attachment of fluorescent labels, e.g. Smith et al., *Nucleic Acids Research*, Vol. 13, pgs. 2399–2412 (1985), and Connolly et al., *Nucleic Acids Research*, Vol. 13, pgs. 4485–4502 (1985); and various chemical modifications of the nucleic acid fragments that render them detectable immunochemically or by other affinity reactions, e.g. Tchen et al., *Proc. Natl. Acad. Sci.*, Vol. 81, pgs. 3466–3470 (1984); Richardson et al., *Nucleic Acids Research*, Vol. 11, pgs. 6167–6184 (1983); Langer et al., *Proc. Natl. Acad. Sci.*, Vol. 78, pgs. 6633–6637 (1981); Brigati et al., *Virology*, Vol. 126, pgs. 32–50 (1983); Broker et al., *Nucleic Acids Research*, Vol. 5, pgs. 363–384 (1978); and Bayer et al., *Methods of Biochemical Analysis*, Vol. 26, pgs. 1–45 (1980).

Preferably probes are prepared by nick translation of a fragment of pcD(SRα)-H400 containing all or the major portion of the H400 coding region. For example, pcD(SRα)-H400 is amplified in JM101, isolated by ethidium bromide cesium chloride density gradient equilibrium centrifugation, digested with BamHI, and the restriction fragment carrying the entire coding region for H400 is separated by gel electrophoresis. The fragment containing the coding region (which is readily identified by a size marker) is extracted from the gel and nick translated in the presence of one or more kinds of labeled nucleotides, e.g. Maniatis et al., *Molecular Cloning: A Laboratory Manual* (Cold Spring Harbor Laboratory, New York, 1982); or Brigati et al. (cited above). After removal of unincorporated nucleotides, the probe is applied to the anchored mRNA at a concentration in the range of between about 1–50 ng/ml (with a specific activity in the range of about $1-2 \times 10^8$ cpm/μg probe).

Peripheral blood lymphocytes (PBLs) (which contain about 80% T cells) are used as a source of T cells for the assay. PBLs are obtained by standard techniques, e.g. Boyum, *Scand. J. Clin. Lab. Invest.*, Vol. 21 (Suppl. 97), pg. 77 (1968). If desired, a fraction of cells enriched in T cells (to about 95%) can be obtained using standard techniques, e.g. eliminating B cells by rosetting, Gmelig-Meyling et al., *Vox Sang.*, Vol. 33, pg. 5 (1977). Generally, PBLs are obtained from fresh blood by Ficoll-Hypaque density gradient centrifugation. Preferably mRNA from PBLs is anchored for hybridization to the probe by the following protocol. Isolated PBLs are lysed by suspending in a lysis buffer (0.14M NaCl, 1.5 mM MgCl$_2$, 10 mM Tris-HCl pH 8.6 , 0.5% Nonidet P-40 (a nonionic detergent, e.g. from Sigma)) at 4° C. at a final concentration of $1 \times 10^8$ cells/ml. The suspension is vortexed for 10 sec and the nuclei are pelleted (13,000 g, 2.5 min). The resulting cytoplasmic lysates are then transferred to a sterile 1.5 ml tube containing 0.3 volumes of 20× SSC (1× SSC=0.15M NaCl, 0.015M trisodium citrate (standard saline citrate)) and 0.2 volumes of 37% (w/w) formaldehyde. The mixture is then incubated at 60° C. for 15 min and stored in aliquots at −70° C. For analysis, 15 μl of each sample is titered by serial three fold dilutions in 15× SSC into a 96-well flat-bottomed microtiter plate (Falcon, Becton Dickinson, Oxnard, CA) in a 0.1 ml. Each dilution is applied with suction to a sheet of Nytran (a modified nylon support available from Schleicher and Schuell, Keene, NH; 0.45 μm pore size) supported on a filter paper (Whatman 3 mmChr, Whatman Inc., Clifton, N.J.) utilizing a 96 hold Minifold apparatus (Schleicher and Schuell). The Nytran paper is then baked (80° C., 2 H) and treated with a prehybridization solution consisting of 50% formamide (BRL, Gaithersburg, MD) 6× SSC, 50 μg/ml *E. coli* tRNA (Sigma), 0.2% (w/v) each of ficoll ($M_w$=400,000), polyvinylpyrollidone, and bovine serum albumin (BSA). The probe is applied to the Nytran support at a concentrate of about 50 ng probe/ml of prehybridization solution. Following hybridization, the support is washed two times for 15 min each at room temperature in 2× SSC, then twice for 30 min each at 60° C. in 2× SSC/0.5% SDS. The support is then exposed to film using an intensifying screen and quantitated by scanning with a laser densitometer (e.g. Ultroscan XL, LKB Instruments Inc., Gaithersburg, MD).

If cytoplasmic dot hybridization lacks sufficient sensitivity, preferably the RNA is first extracted from the PBLs prior to blotting. For example, RNA may be extracted by the guanidinium thiocyanate method disclosed by Chirgwin et al., in *Biochemistry*, Vol. 18, pgs. 5294–5299 (1979).

The descriptions of the foregoing embodiments of the invention have been presented for the purpose of illustration and description. They are not intended to be exhaustive or to limit the invention to the precise forms disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

Applicants have deposited *E. coli* JM101 carrying pcD(SRα)-H400 with the American Type Culture Collection, Rockville, MD, USA (ATCC), under accession number 67614. This deposit was made under conditions as provided under ATCC's agreement for Culture Deposit for Patent Purposes, which assures that the deposit will be made available to the U. S. Commissioner of Patents and Trademarks pursuant to 35 USC 122 and 37 CFR 1.14, and will be made available to the public upon issue of a U.S. patent, which requires that the deposit be maintained. Availability of the deposited strain is not to be construed as a license to practice the invention in contravention of the rights granted under the authority of any government in accordance with its patent laws.

We claim:

1. A nucleic acid capable of encoding the mature polypeptide of the open reading frame defined by the following amino acid sequence:

Lys—Leu—Cys—Val—Thr—Val—Leu—Ser—Leu—
Leu—Met—Leu—Val—Ala—Ala—Phe—Cys—Ser—
Pro—Ala—Leu—Ser—Ala—Pro—Met—Gly—Ser—
Asp—Pro—Pro—Thr—Ala—Cys—Cys—Phe—Ser—
Tyr—Thr—Ala—Arg—
Lys—Leu—Pro—Arg—Asn—Phe—Val—Val—Asp—
Tyr—Tyr—Glu—Thr—Ser—Ser—Leu—Cys—Ser—
Gln—Pro—Ala—Val—Val—Phe—Gln—Thr—Lys—
Arg—Ser—Lys—Gln—Val—Cys—Ala—Asp—Pro—
Ser—Glu—Ser—Trp—Val—Gln—Glu—Tyr—Val—
Tyr—Asp—Leu—Glu—Leu—Asn.

2. The nucleic acid of claim 1 defined by the following nucleotide sequence:

ATG—AAG—CTC—TGC—GTG—ACT—GTC—CTG—
TCT—CTC—CTC—ATG—CTA—GTA—GCT—GCC—
TTC—TGC—TCT—CCA—GCG—CTC—TCA—GCA—
CCA—ATG—GGC—TCA—GAC—CCT—CCC—ACC—
GCC—TGC—TGC—TTT—TCT—TAC—ACC—GCG—
AGG—AAG—CTT—CCT—CGC—AAC—TTT—GTG—
GTA—GAT—TAC—TAT—GAG—ACC—AGC—AGC—
CTC—TGC—TCC—CAG—CCA—GCT—GTG—GTA—
TTC—CAA—ACC—AAA—AGA—AGC—AAG—CAA—
GTC—TGT—GCT—GAT—CCC—AGT—GAA—TCC—
TGG—GTC—CAG—GAG—TAC—GTG—TAT—GAC—
CTG—GAA—CTG—AAC.

* * * * *